United States Patent [19]
Dack et al.

[11] Patent Number: 6,090,852
[45] Date of Patent: Jul. 18, 2000

[54] SUBSTITUTED ALPHA-AMINOSULPHONYL-ACETOHYDROXAMIC ACIDS AS THERAPEUTIC AGENTS

[75] Inventors: Kevin Neil Dack; Gavin Alistair Whitlock, both of Sandwich, United Kingdom

[73] Assignee: Pfizer Inc, New York, N.Y.

[21] Appl. No.: 09/233,883

[22] Filed: Jan. 20, 1999

[30] Foreign Application Priority Data

Jan. 27, 1998 [GB] United Kingdom .................. 9801690

[51] Int. Cl.[7] .......................... A61K 31/16; C07C 239/08
[52] U.S. Cl. ......................... 514/575; 514/451; 514/461; 514/467; 514/520; 514/821; 514/824; 514/825; 549/426; 549/451; 549/491; 562/621; 562/623; 558/411
[58] Field of Search .................. 562/621, 623; 514/575, 461, 467, 451, 520, 825, 821, 824; 558/411; 549/426, 451, 491

[56] References Cited

U.S. PATENT DOCUMENTS 5,932,595  8/1999  Bender et al. ........................ 514/317

FOREIGN PATENT DOCUMENTS 0606046  7/1994  European Pat. Off. .
9535275  12/1995  WIPO .
9902493  1/1999  WIPO .
9929667  6/1999  WIPO .

OTHER PUBLICATIONS

Beckett, R.P., et al., 1996, DDT 1(1):16–26, "Recent advances in matrix metalloproteinase inhibitor research".
Beckett, R.P., 1996, Exp. Opin. Ther. Patents 6(12):1305–1315, "Recent advances in the field of matrix metalloproteinase inhibitors".
Zask, A., et al., 1996, Curr. Pharm. Design 2:624–661, "Inhibition of matrix metalloproteinases: structure based design".

*Primary Examiner*—Shailendra Kumar
*Attorney, Agent, or Firm*—Peter C. Richardson; Paul H. Ginsburg; Alan L. Koller

[57] ABSTRACT

Compounds of formula (I):

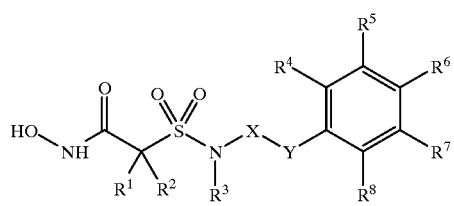

where the substituents are as defined herein, and salts thereof, are matrix metalloprotease inhibitors.

21 Claims, No Drawings

SUBSTITUTED ALPHA-AMINOSULPHONYL-ACETOHYDROXAMIC ACIDS AS THERAPEUTIC AGENTS

This invention relates to a series of substituted α-aminosulphonyl-acetohydroxarmic acids which are inhibitors of zinc-dependent metalloprotease enzymes. In particular, the compounds are inhibitors of certain members of the matrix metalloprotease (MAP) family.

Matrix metalloproteases (MMPs) constitute a family of structurally similar zinc-containing metalloproteases, which are involved in the remodelling and degradation of extracellular matrix proteins, both as part of normal physiological processes and in pathological conditions. Since they have high destructive potential, MMPs are usually under close regulation and failure to maintain MMP regulation has been implicated as a component of a number of diseases and conditions including pathological conditions, such as atherosclerotic plaque rupture, heart failure, restenosis, periodontal disease, tissue ulceration, wound repair, cancer metastasis, tumour angiogenesis, age-related macular degeneration, fibrotic disease, rheumatoid arthritis, osteoarthritis and inflammatory diseases dependent on migratory inflammatory cells.

Another important function of certain MMPs is to activate various enzymes, including other MMPs, by cleaving the pro-domains from their protease domains. Thus some MMPs act to regulate the activities of other MMPs, so that over-production of one MMP may lead to excessive proteolysis of extracellular matrix by another. Moreover, MMPs have different substrate preferences (shown in the following Table for selected family members) and different functions within normal and pathological conditions. For recent reviews of MMPs, see Current Pharmaceutical Design, 1996, 2, 624 and Exp. Opin. Ther. Patents, 1996, 6, 1305.

TABLE

| Enzyme | Other Names | Preferred Substrates |
| --- | --- | --- |
| MMP-1 | collagenase-1; interstitial collagenase | collagens I, II, III, VII, X; gelatins |
| MMP-2 | gelatinase A; 72kDa gelatinase | gelatins; collagens IV, V, VII, X; elastin; fibronectin; activates pro- |
| MMP-3 | stromelysin-1 | proteoglycans; larninin; fibronectin; gelatins |
| MMP-8 | collagenase-2; neutropbil collagenase | collagens I, II, Ill |
| MMP-9 | gelatinase B; 92kDa gelatinase | gelatins; collagens IV, V; elastin |
| MMP-13 | collagenase-3 | collagens I, II, lII; gelatins |
| MMP-14 | MT-MMP-1 | activates pro-MMP-2 & 13; gelatins |

Excessive production of MMP-3 is thought to be responsible for pathological tissue breakdown which underlies a number of diseases and conditions. For example, MMP-3 has been found in the synovium and cartilage of osteoarthritis and rheumatoid arthritis patients, thus implicating MMP-3 in the joint damage caused by these diseases: see Biochemistry, 1989, 28, 8691 and Biochem. J., 1989, 258, 115. MMP-13 is also thought to play an important role in the pathology of osteoarthritis and rheumatoid arthritis: see Lab. Invest., 1997, 76, 717 and Arthritis Rheum., 1997, 40 1391. The compounds of the present invention inhibit both MMP-3 and MMP-13 and thus may be of utility in treating these diseases.

The over-expression of MMP-3 has also been implicated in the tissue damage and chronicity of chronic wounds, such as venous ulcers, diabetic ulcers and pressure sores: see Brit. J. Dermatology, 1996, 135, 52.

Furthermore, the production of MMP-3 may also cause tissue damage in conditions where there is ulceration of the colon (as in ulcerative colitis and Crohn's disease: see J. Immunol., 1997 158, 1582 and J. Clin. Pathol., 1994, 47 113) or of the duodenum (see Am. J. Pathol., 1996, 148, 519).

Moreover, MMP-3 is also thought to be involved in skin diseases such as dystrophic epidermolysis bullosa (see Arch. Dermatol. Res., 1995, 287, 428) and dermatitis herpetiformis (see J. Invest. Dermatology, 1995, 105, 184).

Rupture of atherosclerotic plaques by MMP-3 has also been described (see e.g. Circulation, 1997, 96, 396). Thus, MMP-3 inhibitors may find utility in the treatment of conditions caused by or complicated by embolic phenomena such as cardiac or cerebral infarctions.

Studies of human cancers have shown that MMP-2 is activated on the invasive tumour cell surface (see J. Biol. Chem., 1993, 2, 14033) and BB-94, a non-selective peptidic hydroxamate MMP inhibitor, has been reported to decrease the tumour burden and prolong the survival of mice carrying human ovarian carcinoma xenografts (see Cancer Res., 1993, 53, 2087). Certain compounds of the present invention inhibit MMP-2 and therefore may be useful in the treatment of cancer metastasis and tumour angiogenesis.

Various series of MMP inhibitors have appeared in the literature which have a carbonyl moiety (CO) and a sulphone moiety ($SO_2$) with a two atom "spacer" interposed between them. For example, α-arylsulphonamido-substituted acetohydroxamic acids are disclosed in EP-A-0606046, WO-A-9627583 and WO-A-9719068, whilst EP-A-0780386 discloses certain related sulphone-substituted hydroxamic acids.

The compounds of the present invention represent a new class of compounds, and are inhibitors of some of the members of the MMP family. In particular, they are potent inhibitors of MMP-3 and MMP-13, with certain compounds exhibiting varying degrees of selectivity over other MMPs, such as MMP-1, MMP-2 and MMP-9. Certain of the compounds are potent MMP-2 inhibitors.

Thus, according to one aspect of the present invention, there is provided a compound of formula (I):

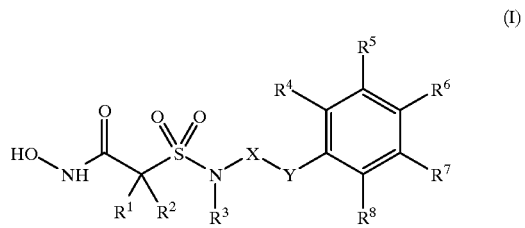

(I)

and a pharmaceutically- and/or veterinarily-acceptable salt thereof, and a solvate of such compound and salt, wherein $R^1$ and $R^2$ are each independently H,
$C_{2-6}$ alkenyl, aryl($C_{1-6}$ alkyl), heteroaryl($C_{1-6}$ alkyl), aryloxy($C_{>4}$ alkyl), heteroaryloxy($C_{1-6}$ alkyl),
$C_{1-6}$ alkyl optionally substituted by $NH_2$, $C_{2-6}$ acylamino, OH, or by $CO_2H$,
or $R^1$ and $R^2$ can be taken together with the carbon atom to which they are attached, to form a 4- to 8-membered saturated carbocyclic or heterocyclic ring, which heterocyclic ring has 1 or 2 hetero-groups selected from O, $S(O)_n$ or $NR^9$ in the ring,
$R^3$ is H, $C_{1-6}$ alkyl or ($C_{1-6}$ alkoxy)$C_{1-6}$ alkyl,
$R^4$, $R^5$, $R^7$ and $R^8$ are each independently H, $C_{1-6}$ alkyl, $C_{1-6}$ alkoxy, CN or halogen, $R^6$ is H, aryl, heteroaryl, aryloxy or heteroaryloxy, $C_{1-6}$ alkyl, $C_{1-6}$ alkoxy, CN or halogen, $R^9$ is H or $C_{1-6}$ alkyl, n is 0, 1 or 2, X is $C_{1-6}$ alkylene or $C_{2-6}$ alkenylene, Y is a direct link, CH=CH or O, wherein "aryl" is phenyl optionally fused with another ring selected from furan, dioxolan, and pyran, which group is optionally mono- or disubstituted by substituents independently seleceted from halogen, CN, $C_{1-6}$ alkyl optionally substituted by OH or $NH_2$, $C_{1-6}$ alkoxy, perfluoro($C_{1-6}$ alkyl) and perfluoro($C_{1-6}$ alkoxy), and wherein "heteroaryl" is a 5- or 6-membered aromatic heterocycle with one or two heteroatoms in the ring, which heteroatoms are independently selected from 0, N and S, which heteroaryl is optionally mono- or disubstituted by substituents independently selected from halogen, CN, $C_{1-6}$ alkyl optionally substituted by OH or $NH_2$, $C_{1-6}$ alkoxy, perfluoro($C_{1-6}$ alkyl) and perfluoro($C_{1-6}$ alkoxy).

In the above definition, unless otherwise indicated, alkyl, alkenyl, alkylene and alkenylene groups having three or more carbon atoms may be straight chain or branched chain.

The compounds of formula (I) may contain one or more chiral centres and therefore can exist as stereoisomers, i.e. as enantiomers or diastereoisomers, as well as mixtures thereof. The invention includes both the individual stereoisomers of the compounds of formula (I) and any mixture thereof. Separation of diastereoisomers may be achieved by conventional techniques, e.g. by fractional crystallisation or chromatography (including HPLC) of a diastereoisomeric mixture of a compound of formula (I) or a suitable salt or derivative thereof. An individual enantiomer of a compound of formula (I) may be prepared from a corresponding optically pure intermediate or by resolution, either by HPLC of the racemate using a suitable chiral support or, where appropriate, by fractional crystallisation of the diastereoisomeric salts formed by reaction of the racemate with a suitable optically active base or acid, as appropriate to the specific compound to be resolved. Furthermore, compound of formula (I) which contain alkenyl groups can exist as cis- or trans- geometric isomers. Again, the invention includes both the separated individual geometric isomers as well as mixtures thereof.

Also included in the invention are radiolabelled derivatives of compounds of formula (I) which are suitable for biological studies.

The pharmaceutically acceptable salts of the compounds of the formula (I) include the acid addition and the base salts thereof.

Suitable acid addition salts are formed from acids which form non-toxic salts and examples are the hydrochloride, hydrobromide, hydroiodide, sulphate, hydrogen sulphate, nitrate, phosphate, hydrogen phosphate, acetate, maleate, famarate, lactate, tartrate, citrate, gluconate, succinate, benzoate, methanesulphonate, benzenesulphonate and p-toluenesulphonate salts.

Suitable base salts are formed from bases which form non-toxic salts and examples are the aluminium, calcium, lithium, magnesium, potassium, sodium, zinc and diethanolamine salts.

For a review on suitable salts see Berge et al, J. Pharm. Sci., 66, 1-19 (1977).

Preferably $R^1$ is H.

Preferably $R^2$ is H.

Preferably $R^3$ is H or $C_{1-6}$ alkyl.

More preferably $R^3$ is H or $CH_3$.

Preferably $R^4$ is H.

Preferably $R^5$ is H or $C_{1-6}$ alkyl.

More preferably $R^5$ is H or $CH_3$.

Preferably $R^6$ is H, $aryl^1$ or $aryl^1$ oxy wherein "$aryl^1$" is phenyl optionally mono- or disubstituted by substituents selected from halogen and CN.

More preferably $R^6$ is H, $aryl^2$ or $aryl^2$ oxy wherein "$aryl^2$" is phenyl optionally 4-substituted by substituents selected from Cl and CN.

Most preferably $R^6$ is H, phenyl, phenoxy, 4-cyanophenyl or 4-chlorophenyl.

Preferably $R^7$ is H.

Preferably $R^8$ is H.

Preferably X is $CH_2$, $(CH_2)_2$, $(CH_2)_3$, or is $CH_2CH=CH$ wherein the terminal methinyl carbon of this group is linked to the Y moiety.

A preferred group of compounds, salts and solvates is that in which at least two of the groups $R^4$, $R^5$, $R^7$ and $R^8$ are all H.

Another preferred group of compounds, salts and solvates is that in which $R^4$, $R^7$ and $R^8$ are all H and $R^5$ is $CH_3$.

Yet another preferred group of compounds, salts and solvates is that in which $R^1$, $R^2$, $R^4$, $R^7$ and $R^8$ are all H, $R^3$ is H or $CH_3$, $R^5$ is H or $CH_3$, $R^6$ is H, phenyl, phenoxy, 4-cyanophenyl or 4-chlorophenyl, X is $CH_2$, $(CH_2)_2$, $(CH_2)_3$, or $CH_2CH=CH$, and the salts and solvates thereof.

The most preferred compounds, salts and solvates are those of the Examples and the salts and solvates thereof.

The invention further provides synthetic methods for the production of compounds, salts and solvates of the invention, which are described below and in the Examples. The skilled man will appreciate that the compounds, salts and solvates of the invention could be made by methods other than those herein described, by adaptation of the methods herein described and/or adaptation of methods known in the art, for example the art described herein.

In the Methods below, unless otherwise specified, the substituents are as defined above with reference to the compounds of formula (I).

Where desired or necessary, the compound of formula (I) can be converted into a pharmaceutically or veterinarily acceptable salt thereof, conveniently by mixing together solutions of a compound of formula (I) and the desired acid or base, as appropriate. The salt may be precipitated from solution and collected by filtration, or may be collected by other means such as by evaporation of the solvent. In some cases, the salt may be the direct product of a reaction to make a compound or salt of the invention in a solvent, in which case no further transformation step would be necessary.

Where desired or necessary, solvates of the compounds and salts of the invention may be made by standard methods well known in the art. In some cases, the solvate may be the direct product of a reaction to make a compound or salt of the invention, in which case no further transformation step would be necessary.

It is to be understood that the synthetic transformation methods mentioned herein may be carried out in various different sequences in order that the desired compounds can be efficiently assembled. The skilled chemist will exercise his judgement and skill as to the most efficient sequence of reactions for synthesis of a given target compound.

It will be apparent to those skilled in the art that sensitive functional groups may need to be protected and deprotected during synthesis of a compound of the invention. This may be achieved by conventional methods, for example as described in "Protective Groups in Organic Synthesis" by T W Greene and P G M Wuts, John Wiley & Sons Inc (1991).

The following processes are illustrative of the general synthetic procedures which may be adopted in order to obtain the compounds of the invention.

Unless otherwise stated, the substituents of the intermediates described below are as defined above for formula (I).

A compound of formula (I) may be prepared directly from an acid derivative of formula (II):

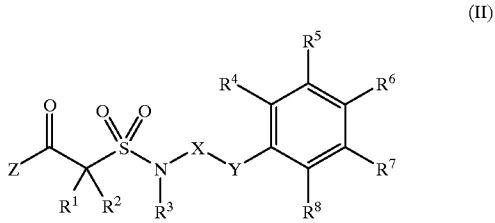

(II)

where Z is chloro, bromo, iodo, $C_{1-3}$ alkyloxy or HO.

When prepared directly from the ester of formula (II), where Z is $C_{1-3}$ alkyloxy, the reaction may be carried out by treatment of the ester with hydroxylamine, preferably up to a 3-fold excess of hydroxylamine, in a suitable solvent at from about room temperature to about 85° C. The hydroxylamine is conveniently generated in situ from a suitable salt such as its hydrochloride salt by conducting the reaction in the presence of a suitable base such as an alkali metal carbonate or bicarbonate, e.g. potassium carbonate. Preferably the solvent is a mixture of methanol and tetrahydrofuran and the reaction is temperature is from about 65 to 70° C.

Alternatively, the ester (II, where Z is $C_{1-3}$ alkyloxy) may be converted by conventional hydrolysis to the corresponding carboxylic acid (II, Z is HO) which is then transformed to the required hydroxamic acid of formula (I).

Preferably the hydrolysis of the ester is effected under basic conditions using up to about a 6-fold excess of an alkali metal hydroxide in aqueous solution, optionally in the presence of a co-solvent, at from about room temperature to about 85° C. Typically the co-solvent is a mixture of methanol and tetrahydroftran or a mixture of methanol and 1,4-dioxan and the reaction temperature is from about 40 to about 70° C.

The subsequent coupling step may be achieved using conventional amide-bond forming techniques, e.g. via the acyl halide derivative (II, Z is Cl, I or Br) and hydroxylamine hydrochloride in the presence of an excess of a tertiary amine such as triethylamine or pyridine to act as acid-scavenger, optionally in the presence of a catalyst such as 4-dimethylaminopyridine, in a suitable solvent such as dichloromethane, at from about 0° C. to about room temperature. For convenience, pyridine may also be used as the solvent.

In particular, any one of a host of amino acid coupling variations may be used. For example, the acid of formula (II) wherein Z is HO may be activated using a carbodiimide such as 1,3-dicyclohexylcarbodiimide or 1-ethyl-3-(3-dimethylaminoprop-1-yl)carbodiimide optionally in the presence of 1-hydroxybenzotriazole and/or a catalyst such as 4-dimethylaminopyridine, or by using a halotrisaminophosphonium salt such as bromotris(pyrrolidino)-phosphonium hexafluorophosphate. Either type of coupling is conducted in a suitable solvent such as dichloromethane or dimethylformamide, optionally in the presence of a tertiary amine such as N-methylmorpholine or N-ethyldiisopropylamine (for example when either the hydroxylamine or the activating reagent is presented in the form of an acid addition salt), at from about 0° C. to about room temperature. Typically, from 1.1 to 2.0 molecular equivalents of the activating reagent and from 1.0 to 4.0 molecular equivalents of any tertiary amine present are employed.

A preferred reagent for mediating the coupling reaction is O-(7-azabenzotriazol-1-yl)-1,1,3,3-tetramethyluronium hexafluorophosphate (HATU).

Preferably a solution of the acid (II, Z is HO) and N-ethyldiisopropylamine in a suitable solvent such as anhydrous dimethylformamide or anhydrous 1-methylpyrrolidin-2-one, under nitrogen, is treated with up to a 1.5-fold excess of HATU at about room temperature followed, after about 15 to 30 minutes, with up to about a 3-fold excess of hydroxylamine hydrochloride and up to about a 4-fold excess of N-ethyldiisopropylamine, optionally in the same solvent, at the same temperature.

An ester of formula (II, Z is $C_{1-3}$ alkyloxy) may be prepared from an amine of formula (III) by sulphonylation with a compound of formula (IV), wherein $R^{10}$ is $C_{1-3}$ alkyloxy and $Z^1$ is a leaving group such as Br, I or Cl.

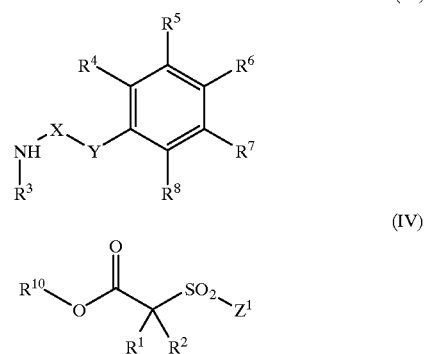

Preferably, $Z^1$ is chloro.

The reaction may be effected in the presence of an appropriate base in a suitable solvent at from about 0° C. to about room temperature. For example, when both $R^1$ and $R^2$ are hydrogen, an appropriate base is 1,8-diazabicyclo[5.4.0] undec-7-ene and a suitable solvent is dichloromethane.

Certain esters of formula (II, Z is $C_{1-3}$ alkyloxy) wherein at least one of $R^1$ and $R^2$ is other than hydrogen may be conveniently obtained from the α-carbanion of an ester of formula (II) wherein at least one of $R^1$ and $R^2$ is hydrogen by conventional C-alkylation procedures using an alkylating agent of formula (VA) or (VB):

(VA)

(VB)

wherein R is as previously defined for $R^1$ or $R^2$ but is not hydrogen, $Z^2$ and $Z^3$ may be the same or different and are suitable leaving groups such as chloro, bromo, iodo, $C_1$–$C_4$ alkanesulphonyloxy, trifluoromethanesulphonyloxy or arylsulphonyloxy (e.g. benzenesulphonyloxy or p-toluenesulphonyloxy), and q is 3, 4, 5, 6 or 7.

Preferably, $Z^2$ and $Z^3$ are selected from bromo, iodo and p-toluenesulphonyloxy.

The carbanion may be generated using an appropriate base in a suitable solvent. Typical base-solvent combinations may be selected from lithium, sodium or potassium hydride, lithium, sodium or potassium bis(trimethylsilyl)amide, lithium diisopropylamide and butyllithium, together with toluene, ether, 1,2-dimethoxyethane, tetrahydrofuran, 1,4-dioxan, dimethylformamide, N,N-dimethylacetamide, 1-methylpyrrolidin-2-one and any mixture thereof.

Preferably the base is sodium hydride and the solvent is dimethylformamide, optionally with tetrahydrofuran as co-solvent, or 1-methylpyrrolidin-2-one. For monoalkylation up to about a 10% excess of base is employed whilst, for dialkylation, from about 2 to about 3 molar equivalents are generally appropriate.

Typically, the carbanion is generated at about room temperature, under nitrogen, and subsequently treated with the required alkylating agent at the same temperature. Clearly, when dialkylation is required and $R^1$ and $R^2$ are different, the substituents may be introduced in tandem in a "one-pot reaction" or in separate steps.

An amine of formula (III) may be obtained by standard chemical procedures. Other amines of formula (III), when neither commercially available nor subsequently described, can be obtained either by analogy with the processes described in the Preparations section below or by conventional synthetic procedures, in accordance with standard textbooks on organic chemistry or literature precedent, from readily accessible starting materials using appropriate reagents and reaction conditions.

Moreover, persons skilled in the art will be aware of variations of, and alternatives to, those processes described hereinafter in the Examples and Preparations sections which allow the compounds defined by formula (I) to be obtained.

The biological activities of the compounds of the present invention were determined by the following test methods, which are based on the ability of the compounds to inhibit the cleavage of various fluorogenic peptides by MMPs 1, 2, 3, 9, 13 and 14.

The assays for MMPs 2, 3, 9 and 14 are based upon the original protocol described in fed.Euro.Biochem.Soc., 1992, 2926 263, with the minor modifications described below.

Inhibition of MMP-1
Enzyme Preparation

Catalytic domain MMP-1 was prepared in Pfizer Central Research laboratories. A stock solution of MMP-1 (1 $\mu$M) was activiated by the addition of aminophenylmercuric acetate (APMA), at a final concentration of 1 mM, for 20 minutes at 37° C. MMP-1 was then diluted in Tris-HCl assay buffer (50 mM Tris, 200 mM NaCl, 5 mM $CaCl_2$, 2 $\mu$M $ZnSO_4$ and 0.05% Brij 35, pH 7.5) to a concentration of 10 nM. The final concentration of enzyme used in the assay was 1 nM.

Substrate

The fluorogenic substrate used in this assay was Dnp—Pro-β-cyclohexyl—Ala—Gly—Cys(Me)—His—Ala—Lys—(N—Me—Ala)—$NH_2$ as originally described in Anal. Biochem., 1993, 212, 58. The final substrate concentration used in the assay was 10 $\mu$M.

Determination of Enzyme Inhibition

The test compound was dissolved in dimethyl sulphoxide and diluted with assay buffer so that no more than 1% dimethyl sulphoxide was present. Test compound and enzyme were added to each well of a 96 well plate and allowed to equilibrate for 15 minutes at 37° C. in an orbital shaker prior to the addition of substrate. Plates were then incubated for 1 hour at 37° C. prior to determination of fluorescence (substrate cleavage) using a fluorimeter (Fluostar; BMG LabTechnologies, Aylesbury, UK) at an excitation wavelength of 355 nm and emission wavelength of 440 nm. The potency of inhibition was measured from the amount of substrate cleavage obtained using a range of test compound concentrations and, from the resulting dose-response curve, an $IC_{50}$ value (the concentration of inhibitor required to inhibit 50% of the enzyme activity) was calculated.

Inhibition of MMP-2, MMP-3 and MMP-9
Enzyme Preparation

Catalytic domains MMP-2, MMP-3 and MMP-9 were prepared in Pfizer Centrai Research laboratories. A stock solution of MMP-2, MMP-3 or MMP-9 (1 $\mu$M) was activated by the addition of APMA. For MMP-2 and MMP-9, a final concentration of 1 mM APMA was added, followed by incubation for 1 hour at 37° C. MMP-3 was activated by the addition of 2 mM APMA, followed by incubation for 3 hours at 37° C. The enzymes were then diluted in Tris-HCl assay buffer (100 mM Tris, 100 mM NaCl, 10 mM $CaCl_2$ and 0.16% Brij 35, pH 7.5) to a concentration of 10 nM. The final concentration of enzyme used in the assays was 1 nM.

Substrate

The fluorogenic substrate used in this screen was Mca—Arg—Pro—Lys—Pro—Tyr—Ala—Nva—Trp—Met—Lys (Dnp)—$NH_2$ (Bachem Ltd., Essex, UK) as originally described in J.Biol.Chem., 1994, 269, 20952. This substrate was selected because it has a balanced hydrolysis rate against MMPs 2, 3 and 9 ($k_{cat}/k_m$ of 54,000, 59,400 and 55,300 $s^{-1} M^{-1}$ respectively). The final substrate concentration used in the assay was 5 $\mu$M.

Determination of Enzyme Inhibition

The test compound was dissolved in dimethyl sulphoxide and diluted with assay buffer so that no more than 1% dimethyl sulphoxide was present. Test compound and enzyme were added to each well of a 96 well plate and allowed to equilibrate for 15 minutes at 37° C. in an orbital shaker prior to the addition of substrate. Plates were then incubated for 1 hour at 37° C., prior to determination of fluorescence using a fluorimeter (Fluostar; BMG LabTechnologies, Aylesbury, UK) at an excitation wavelength of 328 nm and emission wavelength of 393 nm. The potency of inhibition was measured from the amount of substrate cleavage obtained using a range of test compound concentrations and, from the resulting dose-response curve, an $IC_{50}$ value (the concentration of inhibitor required to inhibit 50% of the enzyme activity) was calculated.

Inhibition of MMP-13
Enzyme Preparation

Human recombinant MMP-13 was prepared by PanVera Corporation (Madison, Wis.) and characterised at Pfizer Central Research laboratories. A 1.9 mg/ml stock solution was activated with 2 mM APMA for 2 hours at 37° C. MMP-13 was then diluted in assay buffer (50 mM Tris, 200 mM NaCl, 5 mM $CaCl_2$, 20 $\mu$M $ZnCl_2$ and 0.02% Brij 35, pH 7.5) to a concentration of 5.3 nM. The final concentration of enzyme used in the assay was 1.3 nM.

Substrate

The fluorogenic substrate used in this screen was Dnp—Pro—Cha—Gly—Cys(Me)—His—Ala—Lys(NMA)—$NH_2$. The final substrate concentration used in the assay was 10 $\mu$M.

Determination of Enzyme Inhibition

The test compound was dissolved in dimethyl sulphoxide and diluted with assay buffer so that no more than 1% dimethyl sulphoxide was present. Test compound and enzyme were added to each well of a 96 well plate. The addition of substrate to each well initiated the reaction.

Fluorescence intensity was determined using a 96 well plate fluorimeter (Cytofluor II; PerSeptive Biosystems, Inc., Framingham, Mass.) at an excitation wavelength of 360 nm and emission wavelength of 460 nm. The potency of inhibition was measured from the amount of substrate cleavage obtained using a range of test compound concentrations and, from the resulting dose-response curve, an $IC_{50}$ value (the concentration of inhibitor required to inhibit 50% of the enzyme activity) was calculated.

Inhibition of MMP-14

Enzyme Preparation

Catalytic domain MMP-14 was prepared in Pfizer Central Research laboratories. A 10 μM enzyme stock solution was activated for 20 minutes at 25° C. following the addition of 5 μg/ml of trypsin (Sigma, Dorset, UK). The trypsin activity was then neutralised by the addition of 50 μg/ml of soyabean trypsin inhibitor (Sigma, Dorset, UK), prior to dilution of this enzyme stock solution in Tris-HCl assay buffer (100 mM Tris, 100 nM NaCl, 10 mM $CaCl_2$, 0.16% Brij 35, pH 7.5) to a concentration of 10 nM. The final concentration of enzyme used in the assay was 1 nM.

Substrate

The fluorogenic substrate used in this screen was Mca—Pro—Leu—Gly—Leu—Dpa—Ala—Arg—$NH_2$ (Bachem Ltd., Essex, UK) as described in J.Biol.Chem., 1996, 271, 17119.

Determination of enzyme inhibition

This was performed as described for MMPs 2, 3 and 9.

For use in mammals, including humans, the compounds of formula (I) or their salts or solvates of such compounds or salts, can be administered alone, but will generally be administered in admixture with a pharmaceutically or veterinarily acceptable diluent or carrier selected with regard to the intended route of administration and standard pharmaceutical practice. For example, they can be administered orally, including sublingually, in the form of tablets containing such excipients as starch or lactose, or in capsules or ovules either alone or in admixture with excipients, or in the form of elixirs, solutions or suspensions containing flavouring or colouring agents. The compound or salt could be incorporated into capsules or tablets for targetting the colon or duodenum via delayed dissolution of said capsules or tablets for a particular time following oral administration. Dissolution could be controlled by susceptibility of the formulation to bacteria found in the dudodenum or colon, so that no substantial dissolution takes places before reaching the target area of the gastrointestinal tract. The compounds or salts can be injected parenterally, for example, intravenously, intramuscularly or subcutaneously. For parenteral administration, they are best used in the form of a sterile aqueous solution or suspension which may contain other substances, for example, enough salt or glucose to make the solution isotonic with blood. They can be administered topically, in the form of sterile creams, gels, suspensions, lotions, ointments, dusting powders, sprays, drug-incorporated dressings or via a skin patch. For example they can be incorporated into a cream consisting of an aqueous or oily emulsion of polyethylene glycols or liquid paraffin, or they can be incorporated into an ointment consisting of a white wax soft paraffin base, or as hydrogel with cellulose or polyacrylate derivatives or other viscosity modifiers, or as a dry powder or liquid spray or aerosol with butane/propane, HFA or CFC propellants, or as a drug-incorporated dressing either as a tulle dressing, with white soft paraffin or polyethylene glycols impregnated gauze dressings or with hydrogel, hydrocolloid, alginate or film dressings. The compound or salt could also be administered intraocularly as an eye drop with appropriate buffers, viscosity modifiers (e.g. cellulose derivatives), preservatives (e.g. benzalkonium chloride (BZK)) and agents to adjust tenicity (e.g. sodium chloride). Such formulation techniques are well-known in the art.

For veterinary use, a compound of formula (I), or a veterinarily acceptable salt thereof, or a veterinarily acceptable solvate of either entity, is administered as a suitably acceptable formulation in accordance with normal veterinary practice and the veterinary surgeon will determine the dosing regimen and route of administration which will be most appropriate for a particular animal.

All such formulations may also contain appropriate stabilisers and preservatives.

Reference to treatment includes prophylaxis as well as alleviation of established conditions, or the symptoms thereof.

For oral and parenteral administration to animal (inc. human) patients, the daily dosage level of the compounds of formula (I) or their salts will be from 0.001 to 20, preferably from 0.01 to 20, more preferably from 0.1 to 10, and most preferably from 0.5 to 5 mg/kg (in single or divided doses). Thus tablets or capsules of the compounds will contain from 0.1 to 500, preferably from 50 to 200, mg of active compound for administration singly or two or more at a time as appropriate.

For topical administration to animal (inc. human) patients with chronic wounds, the daily dosage level of the compounds, in suspension or other formulation, could be from 0.00001 to 1mg/ml, preferably from 0.001 to 0.1 mg/ml.

The physician or veterinary surgeon in any event will determine the actual dosage which will be most suitable for a an individual patient and it will vary with the age, weight and response of the particular patient. The above dosages are exemplary of the average case; there can of course be individual instances where higher or lower dosage ranges are merited, and such are within the scope of this invention.

Thus the invention provides a pharmaceutical composition comprising a compound of formula (I), or a pharmaceutically acceptable salt thereof, or a pharmaceutically acceptable solvate of either entity, together with a pharmaceutically acceptable diluent or carrier.

It further provides a veterinary formulation comprising a compound of formula (I), or a veterinarily acceptable salt thereof, or a veterinarily acceptable solvate of either entity, together with a veterinarily acceptable diluent or carrier.

The invention also provides a compound of formula (I), or a pharmaceutically acceptable salt thereof, or a pharmaceutically acceptable solvate of either entity, or a pharmaceutical composition containing any of the foregoing, for use as a human medicament.

In addition, it provides a compound of formula (I), or a veterinarily acceptable salt thereof, or a veterinarily acceptable solvate of either entity, or a veterinary formulation containing any of the foregoing, for use as a medicament for non-human animal.

In yet another aspect, the invention provides the use of a compound of formula (I), or a pharmaceutically acceptable salt thereof, or a pharmaceutically acceptable solvate of either entity, for the manufacture of a human medicament for the treatment of a condition mediated by one or more MMPs.

It also provides the use of a compound of formula (I), or a veterinarily acceptable salt thereof, or a veterinarily acceptable solvate of either entity, for the manufacture of an animal medicament for the treatment of a condition mediated by one or more MMPs.

Moreover, the invention provides the use of a compound of formula (I), or a pharmaceutically acceptable salt thereof, or a pharmaceutically acceptable solvate of either entity, for the manufacture of a human medicament for the treatment of atherosclerotic plaque rupture, myocardial infarction, heart failure, restenosis, stroke, periodontal disease, tissue ulceration, wound repair, skin diseases, cancer metastasis, tumour angiogenesis, age-related macular degeneration, fibrotic disease, rheumatoid arthritis, osteoarthritis and inflammatory diseases dependent on migratory inflammatory cells.

It also provides the use of a compound of formula (I), or a veterinarily acceptable salt thereof, or a veterinarily acceptable solvate containing either entity, for the manufacture of an animal medicament for the treatment of atherosclerotic plaque rupture, myocardial infarction, heart failure, restenosis, stroke, periodontal disease, tissue ulceration, wound repair, skin diseases, cancer metastasis, tumour angiogenesis, age-related macular degeneration, fibrotic disease, rheumatoid arthritis, osteoarthritis and inflammatory diseases dependent on migratory inflammatory cells.

Additionally, the invention provides a method of treating or preventing a medical condition for which a MMP inhibitor is indicated, in an animal such as a mammal (including a human being), which comprises administering to said animal a therapeutically effective amount of a compound of formula (I), or a pharmaceutically or veterinarily acceptable salt thereof, or a pharmaceutically or veterinarily acceptable solvate of either entity, or a pharmaceutical composition or veterinary formulation containing any of the foregoing.

Still further, the invention provides a method of treating or preventing atherosclerotic plaque rupture, myocardial infarction, heart failure, restenosis, stroke, periodontal disease, tissue ulceration, wound repair, skin diseases, cancer metastasis, tumour angiogenesis, age-related macular degeneration, fibrotic disease, rheumatoid arthritis, osteoarthritis and inflammatory diseases dependent on migratory inflammatory cells, in a animal (including a human being), which comprises administering to said animal a therapeutically effective amount of a compound of formula (I), or a pharmaceutically or veterinarily acceptable salt thereof, or a pharmaceutically or veterinarily acceptable solvate of either entity, or a pharmaceutical composition or veterinary formulation containing any of the foregoing.

The invention also includes any novel intermediates described herein, for example those of formula (II).

The syntheses of the compounds of the invention and of the intermediates for use therein are illustrated by the following Examples and Preparations.

EXAMPLES AND PREPARATIONS

Room temperature means 20 to 25° C. Flash chromatography refers to column chromatography on silica gel (Kieselgel 60, 230–400 mesh). Melting points are uncorrected. $^1$H Nuclear magnetic resonance (NMR) spectra were recorded using a Bruker AC300, a Varian Unity Inova-300 or a Varian Unity Inova-400 spectrometer and were in all cases consistent with the proposed structures. Characteristic chemical shifts are given in parts-per-million downfield from tetramethylsilane using conventional abbreviations for designation of major peaks: e.g. s, singlet; d, doublet; t, triplet; q, quartet; m, multiplet; br, broad. Mass spectra were recorded using a Finnigan Mat. TSQ 7000 or a Fisons Intruments Trio 1000 mass spectrometer. LRMS means low resolution mass spectrum and the calculated and observed ions quoted refer to the isotopic composition of lowest mass.-Hexane refers to a mixture of hexanes (hplc grade) b.p. 65–70° C. Ether refers to diethyl ether. Acetic acid refers to glacial acetic acid. 1-Hydroxy-7-aza- 1 H-1,2,3-benzotriazole (HOAt), N-[(dimethylamino)- 1 H-1,2,3-triazolo[4,5-b]pyridin-1-ylmethylene]-N-methylmethaninium hexafluorophosphate N-oxide (HATU) and 7-azabenzotriazol-1-yloxytris(pyrrolidino)phosphonium hexafluorophosphate (PyAOP) were purchased from PerSeptive Biosystems U.K. Ltd.

Example 1

N-Hydroxy 2-({methyl[(biphen-4-yl)methyl]amino}sulfonyl)acetamide

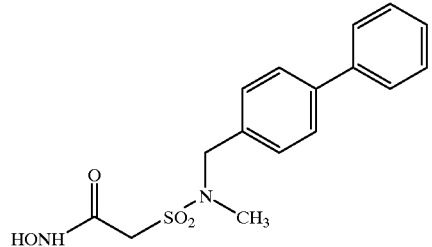

(a) Methyl 2-( {methyl[(biphen4-yl)methyl]amino}sulfonyl)acetate

N-Methyl-N-[(biphen-4-yl)methyl]amine (Preparation 1, 500 mg, 2.5 mmol) and 1,8-diazabicyclo[5.4.0]undec-7-ene (DBU, 0.38 ml, 2.5 mmol) were dissolved in dichloromethane (5 ml) and cooled to 0° C. Methyl chlorosulfonylacetate (0.44 g, 2.5 mmol) in dichloromethane (5 ml) was added dropwise to the solution, and the stirred mixture was allowed to warm to ambient temperature for 20 hours. The mixture was diluted with dichloromethane and washed with aqueous phosphate buffer (at pH 7), dried (MgSO$_4$), and the solvents were evaporated under reduced pressure. The residue was purified by flash chromatography on silica gel (dichloromethane as eluent) and the isolated product was crystallised from diisopropyl ether to give the title compound as a colourless solid (388 mg).

m.p. 82–84° C.

$^1$H NMR (400 MHz, CDCl$_3$): 2.90 (s, 3 H), 3.86 (s, 3 H), 4.05 (s, 2 H), 4.46 (s, 2 H), 7.33–7.40 (m, 1 H), 7.40–7.45 (m, 4 H), 7.54–7.67 (m, 4 H).

LRMS (Thermospray): 334.8 (MH$^+$).

(b) N-Hydroxy-2-({methyl[(biphen-4-yl)methyl]amino}sulfonyl)acetamide

Potassium carbonate (124 mg, 0.9 mmol) was added to a mixture of methyl 2-({methyl[(biphen-4-yl)methyl]amino}sulfonyl)acetate (100 mg, 0.3 mmol) and hydroxylamine hydrochloride (63 mg, 0.9 mmol) in methanol (3 ml). The mixture was heated to reflux for 18 hours. The mixture was cooled and partitioned between ethyl acetate and 0.1 M aqueous hydrochloric acid. The layers were separated, and the organic layer was dried (MgSO$_4$), and the solvents were removed under reduced pressure. The residue was triturated with diisopropyl ether to give the titled compound as a colourless solid (88 mg).

m.p. 176–178° C.

$^1$H NMR (300 MHz, DMSO-d$_6$): 2.75 (s, 3 H), 3.98 (s, 2 H), 4.33 (s, 2 H), 7.33–7.52 (m, 5 H), 7.61–7.74 (m, 4 H), 9.22 (s, 1 H), 10.84 (br s, 1 H).

LRMS (Thermospray): 335.7 (MH$^+$)

Analysis: Found: C, 57.32; H, 5.40; N, 8.24.

$C_{16}H_{18}N_2O_4S$ Requires: C, 57.47; H, 5.43; N, 8.38.

Example 2
N-Hydroxy 2-({[2-(biphen-4-yl)ethyl]amino}sulfonyl) acetamide

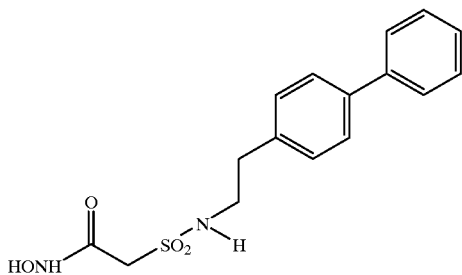

(a) Methyl 2-({[2-(biphen-4-vl)ethyl]amino}sulfonyl) acetate

In a manner similar to Example 1 (a), 2-(biphen4yl) ethylamine (Preparation 2) was reacted with methyl chlorosulfonylacetate to give the title compound as a colourless solid.

m.p. 130–131° C.
$^1$H NMR (300 MHz, CDCl$_3$): 2.97 (t, 2 H), 3.49 (q, 2 H), 3.76 (s, 3 H), 3.93 (s, 2 H), 4.76 (br t, 1 H), 7.22–7.40 (m, 3 H), 7.40–7.50 (m, 2 H), 7.52–7.64 (m, 4 H).
LRMS (Thermospray): 351.1 (MNH$_4^+$)
Analysis: Found: C, 61.39; H, 5.74; N, 4.19.
C$_{17}$H$_{19}$NO$_4$S, Requires: C, 61.24; H, 5.74; N, 4.20.

(b) N-Hydroxy 2-({[2-(biphen4-yl)ethyl]amino}sulfonyl) acetamide

In a manner similar to Example 1 (b), methyl 2-({[2-(biphen4-yl)ethyl]amino}sulfonyl)acetate was reacted with hydroxylamine to give the title compound as a colourless solid.

m.p. 202–204° C.
$^1$H NMR (300 MHz, DMSO-d$_6$): 2.81 (t, 2 H), 3.16–3.29 (m, 2 H), 3.78 (s, 2 H), 7.24–7.39 (m, 3 H), 7.40–7.50 (m, 2 H), 7.54–7.68 (m, 4 H), 9.13 (s, 1 H), 10.74 (br s, 1 H).
LRMS (Thermospray): 336.2 (MH$^+$)
Analysis: Found: C, 57.45; H, 5.40; N, 8.35.
C$_{16}$H$_{18}$N$_2$O$_4$S Requires: C, 57.47; H, 5.43; N, 8.38.

Example 3
N-Hydroxy 2-({[2-(biphen-4-yloxy)ethyl]amino}sulfonyl) acetamide

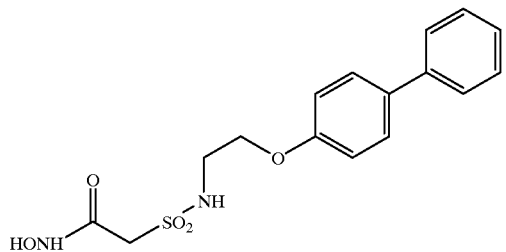

(a) Methyl 2-({[2-(biphen4-yloxy)ethyl]amino}sulfonyl) acetate

In a manner similar to Example 1 (a), 2-(biphen-4-yloxy) ethylamine (Preparation 3) was reacted with methyl chlorosulfonylacetate to give the title compound as a colourless solid.

m.p. 123–124° C.
$^1$H NMR (400 MHz, CDCl$_3$): 3.62 (q, 2 H), 3,79 (s, 3 H), 4.10 (s, 2 H), 4.18 (t, 2 H), 5.26 (br t, 1 H), 6.98 (d, 2 H), 7.31–7.34 (m, 1 H), 7.39–7.46 (m, 2 H), 7.50–7.60 (m, 4 H).

Analysis: Found: C, 58.33; H, 5.44; N, 3.99.
C$_{17}$H$_{19}$NO$_5$S Requires: C, 58.43; H, 5.48; N, 4.01.

(b) N-Hydroxy 2-({[2-biphen-4-yloxy)ethyl] amino}sulfonyl)acetamide

In a manner similar to Example 1 (b), methyl 2-({[2-(biphen-4-yloxy)ethyl]amino}sulfonyl)acetate was reacted with hydroxylamine to give the title compound as a colourless solid.

m.p. 222–224° C.
$^1$H NMR (400 MHz, DMSO-d$_6$): 3.39 (d, 2 H), 3.86 (s, 2 H), 4.07 (t, 2 H), 7.07 (d, 2 H), 7.29–7.33 (m, 1 H), 7.37–7.51 (m, 3 H), 7.57–7.65 (m, 4 H), 9.13 (s, 1 H), 10.73 (s, 1 H).
LRMS (Thermospray): 352.0 (MH$^+$)
Analysis: Found: C, 54.69; H, 5.13; N, 7.92.
C$_{19}$H$_{22}$N$_2$O$_4$S Requires: C, 54.84; H, 5.18; N, 8.00.

Example 4
N-Hydroxy 2-[methyl(phenethyl)amino]sulfonylacetamide

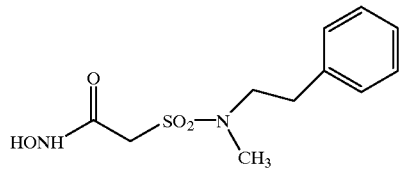

(a) Methyl 2-[methyl(phenethyl)amino]sulfonylacetate

In a manner similar to Example 1 (a), N-methyl-N-phenethylamine was reacted with methyl chlorosulfonylacetate to give the titled compound as a colourless oil.

$^1$H NMR (400 MHz, CDCl$_3$): 2.88–2.96 (m, 5 H), 3.48 (t, 2 H), 3.77 (s, 3 H), 3.81 (s, 2 H), 7.18–7.36 (m, 5 H).

(b) N-Hydroxy 2-[methyl(phenethyl)amino] sulfonylacetamide

In a manner similar to Example 1 (b), methyl 2-[methyl (phenethyl)amino]sulfonyl-acetate was reacted with hydroxylamine to give the title compound as a colourless solid.

m.p. 149–151° C.
$^1$H NMR (300 MHz, DMSO-d$_6$): 2.76–2.86 (m, 5 H), 3.28 (s, 2 H), 3.80 (s, 2 H), 7.15–7.35 (m, 5 H), 9.14 (s, 1 H), 10.73 (s, 1 H).
LRMS (Thermospray): 290.0 (MNH$_4^+$)
C$_{11}$H$_{16}$N$_2$O$_4$S.

Example 5
N-Hydroxy 2-({methyl-[2-(biphen-4-yloxy)ethyl] amino}sulfonyl)acetamide

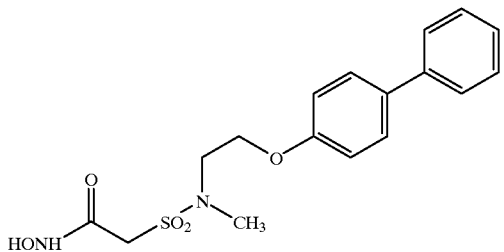

(a) Methyl 2-({methyl-[2-(biphen-4-yloxy)ethyl] amino}sulfonyl)acetate

Sodium hydride (23 mg of 60% dispersion in mineral oil, 0.58 mmol) was added to a stirred solution of methyl 2-({[2-(biphen-4-yloxy)ethyl]amino}sulfonyl)acetate (Example 3 (a), 185 mg, 0.53 mmol) in anhydrous dimethylformamide (2 ml) at ambient temperature under a nitrogen atmosphere. After 30 minutes methyl p-toluenesulfonate (0.99 g, 0.53 mmol) was added, and stirring continued for an additional 3 hours. The mixture was partitioned between ethyl acetate and aqueous phosphate buffer (pH 7). The organic layer was separated and washed with water, dried (MgSO$_4$) and the solvents were removed under reduced pressure. The residue was crystallised from diisopropyl ether to give the titled compound as a colourless solid (170 mg).

m.p. 73–75° C.

$^1$H NMR (400 MHz, CDCl$_3$): d=3.11 (s, 3 H), 3.69 (t, 2 H), 3,78 (s, 3 H), 4.08 (s, 2 H), 4.18 (t, 2 H), 6.97 (d, 2 H), 7.28–7.32 (m, 1 H), 7.38–7.46 (m, 2 H), 7.47–7.58 (m, 4 H).

LRMS (Thermospray): 381.1 (MNH$_4^+$)

Analysis: Found: C, 59.39; H, 5.88; N, 3.74.

C$_{18}$H$_{21}$NO$_5$S Requires: C, 59.48; H, 5.82; N, 3.86.

(b) N-Hydroxy 2-({methyl-[2-biphen-4-yloxy)ethyl]amino}sulfonyl)acetamide

In a manner similar to Example 1 (b), methyl 2-({methyl-[2-(biphen-4-yloxy)ethyl]amino}sulfonyl)acetate was reacted with hydroxylamine to give the title compound as a colourless solid.

m.p. 153–155° C.

$^1$H NMR (400 MHz, DMSO-d$_6$): d=2.93 (s, 3 H), 3.47–3.58 (m, 2 H), 3.90 (s, 2 H), 4.10–4.20 (m, 2 H), 7.03 (d, 2 H), 7.25–7.33 (m, 1 H), 7.37–7.46 (m, 2 H), 7.54–7.66 (m, 4 H), 9.18 (s, 1 H), 10.79 (s, 1 H).

LRMS (APCI): 368.8 (MH$^+$)

Analysis: Found: C, 55.56; H, 5.47; N, 7.24.

C$_{17}$H$_{20}$N$_2$O$_5$S Requires: C, 56.03; H, 5.53; N, 7.69.

Example 6
N-Hydroxy 2-({methyl-[2-(biphen-4-yl)ethyl]amino}sulfonyl)acetamide

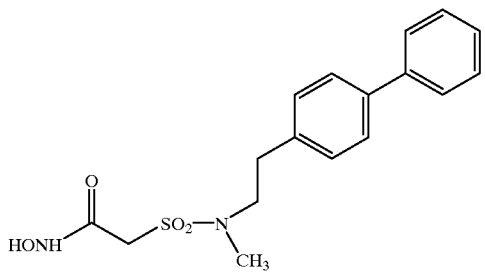

(a) Methyl 2-({methyl-[2-(biphen-4-yl)ethyl]amino}sulfonyl)acetate

In a manner similar to Example 5 (a), methyl 2-({[2-(biphen-4-yl)ethyl]amino}-sulfonyl)acetate (Example 2 (a)) was reacted with sodium hydride and methyl p-toluenesulfonate to give the title compound as a colourless solid.

m.p. 72–74° C.

$^1$H NMR (400 MHz, CDCl$_3$): 2.87–2.97 (m, 5 H), 3.48 (t, 2 H), 3.75 (s, 3 H), 3.82 (s, 2 H), 7.24–7.33 (m, 3 H), 7.37–7.44 (m, 2 H), 7.47–7.59 (m, 4 H).

LRMS (Thermospray): 365.0 (MNH$_4^+$)

C$_{18}$H$_{21}$NO$_4$S (b) N-Hydroxy 2-({methyl-[2-(biphen-4-yl)ethyl]amino}sulfonyl)acetamide In a manner similar to Example 1 (b), methyl 2-({methyl-[2-(biphen-4-yl)ethyl]amino}sulfonyl)acetate was reacted with hydroxylamine to give the title compound as a colourless solid.

m.p. 166–168° C.

$^1$H NMR (400 MHz, DMSO-d$_6$): 2.77–2.88 (m, 5 H), 3.32 (t, 2 H), 3.78 (s, 2 H), 7.24–7.33 (m, 3 H), 7.37–7.45 (m, 2 H), 7.53–7.63 (m, 4 H).

LRMS (Thermospray): 365.9 (MNH$_4^+$)

C$_{17}$H$_{20}$N$_2$O$_4$S.

Example 7
N-Hydroxy 2-({methyl[4-phenoxybenzyl]amino}sulfonyl)acetamide

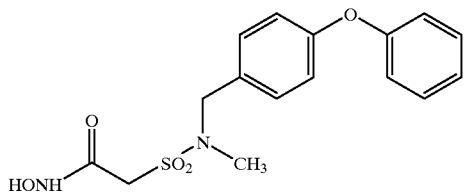

(a) Methyl 2-({methyl[4-phenoxybenzyl]amino}sulfonyl)acetate

In a manner similar to Example 1 (a), N-methyl-N-(4-phenoxybenzyl)amine (Preparation 4) was reacted with methyl chlorosulfonylacetate to give the title compound as a colourless solid.

m.p. 63–64° C.

$^1$H NMR (300 MHz, CDCl$_3$): 2.84 (s, 3 H), 3.81 (s, 3 H), 4.00 (s, 2 H), 4.35 (s, 2 H), 6.95–7.06 (m, 4 H), 7.06–7.16 (m, 1 H), 7.21–7.40 (m, 4 H).

LRMS (Thermospray): 350.6 (MH$^+$)

C$_{17}$H$_{19}$NO$_5$S.

(b) N-Hydroxy 2-({methyl[4-henoxybenzyl]amino}sulfonyl)acetamide

In a manner similar to Example 1 (b), methyl 2-({methyl[4-phenoxybenzyl]amino}-sulfonyl) acetate was reacted with hydroxylamine to give the title compound as a colourless solid.

m.p. 154–157° C.

$^1$H NMR (400 MHz, DMSO-d$_6$): d=2.72 (s, 3 H), 3.95 (s, 2 H), 4.26 (s, 2 H), 6.94–7.04 m, 4 H), 7.10–7.18 (m, 1 H), 7.29–7.43 (m, 4 H).

LRMS (Thermospray): 373.5 (MNa$^+$)

Example 8
-Hydroxy 2-({methyl[(4'-cyanobiphen-4-yl)methyl]amino}sulfonyl)acetamide

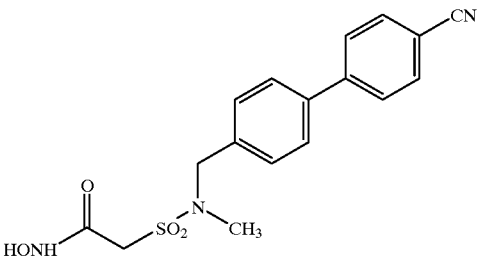

(a) Methyl 2-({methyl[(4-bromophenyl)methyl]amino}sulfonyl)acetate

In a manner similar to Example 1 (a), N-methyl-N-(4-bromobenzyl)amine (Preparation 5) was reacted with methyl chlorosulfonylacetate to give the title compound as a pale yellow oil.

$^1$H NMR (300 MHz, CDCl$_3$): 2.83 (s, 3 H), 3.82 (s, 3 H), 4.03 (s, 2 H), 4.33 (s, 2 H), 7.25 (d, 2 H), 7.50 (d, 2 H).

LRMS (Thermospray): 354.3 (MNH$_4^+$)

C$_{11}$H$_{14}$BrNO$_4$S.

(b) Methyl-2-({methyl[(4'-cyanobiphen-4-yl)methyl]amino}sulfonyl)acetate

To a solution of methyl 2-({methyl[(4-bromophenyl)methyl]amino}sulfonyl)acetate (300 mg, 0.9 mmol) in dimethoxyethane (5 ml) was added 4-cyanophenylboronic acid (Preparation 6, 150 mg, 1.0 mmol), caesium fluoride (290 mg), tri-ortho-tolyl phosphine (28 mg, 0.09 mmol) and bis(benzylideneacetone)palladium(0) (25 mg, 0.04 mmol) and the mixture was heated to reflux for 1 hour under an atmosphere of nitrogen. The mixture was cooled to ambient temperature, diluted with dichloromethane (30 ml) and washed with water. The organic layer was dried (Na$_2$SO$_4$), the solvent was evaporated under reduced pressure and the residue was purified by flash chromatography on silica gel (hexane/ethyl acetate 2:1 as eluent) to give the titled compound as a pale yellow low melting solid (230 mg).

$^1$H NMR (300 MHz, CDCl$_3$): 2.88 (s, 3 H), 3.84 (s, 3 H), 4.06 (s, 2 H), 4.45 (s, 2 H), 7.48 (d, 2 H), 7.60 (d, 2 H), 7.67 (d, 2 H), 7.75 (d, 2 H).

(c) 2-({methyl[(4'-cyanobiphen-4-yl)methyl]amino}sulfonyl)acetic acid

To a solution of methyl-2-({methyl[(4'-cyanobiphen-4-yl)methyl]amino}-sulfonyl)acetate (200 mg, 0.56 nunol) in methanol (2 ml) and tetrahydroflran (5 ml) was added 1 M aqueous sodium hydroxide solution (1.2 ml, 1.2 mmol) and the mixture was stirred at ambient temperature for 2 hours. The solution was diluted with water (10 ml), acidified to pH 2 with 2 M aqueous hydrochloric acid and extracted with dichloromethane (2×30 ml). The combined organic layers were dried (Na$_2$SO$_4$), and the solvent was evaporated under reduced pressure to give the title compound as a pale yellow solid (130 mg).

m.p. 149–152° C.

$^1$H NMR (300 MHz, DMSO-d$_6$): 2.74 (s, 3 H), 4.16 (s, 2 H), 4.57 (s, 2 H), 7.46 (d, 2 H), 7.78 (d, 2 H), 7.87 (d, 2 H), 7.90 (d, 2 H).

(d) N-Hydroxy 2-({methyl[(4'-cyanobiphen-4-yl)methyl]amino}sulfonyl)-acetamide

O-(7-Azabenzotriazol-1-yl)-1,1,3,3-tetramethyluronium hexafluorophosphate (HATU 263 mg, 0.72 mmol) was added to a solution of 2-({methyl[(4'-cyanobiphenyl-4-yl)methyl]amino}sulfonyl)acetic acid (185 mg, 0.48 mmol) and N-ethyl-N,N-diisopropylamine (0.08 ml, 0.48 mmol) in anhydrous dimethylformamide (3 ml) at ambient temperature under an atmosphere of nitrogen. After stirring for 20 minutes a solution of hydroxylamine hydrochloride (131 mg, 1.92 mmol) and N-ethyl-NN-diisopropylamine (0.33 ml, 1.92 mmol) in anhydrous dimethylformamide (1 ml) was added and the solution was stirred for a further 16 hours. The mixture was partitioned between aqueous phosphate buffer (at pH 7) and ethyl acetate. The organic layer was washed with water, dried (MgSO4) and the solvent evaporated under reduced pressure. The residue was purified by flash chromatography on silica gel (dichloromethane/methanol/aqueous ammonia 90:10:1 as eluent) to give the title compound as a colourless solid (14 mg).

m.p. 128–130° C.

$^1$H NMR (400 MHz, DMSO-d$_6$): 2.73 (s, 3 H), 3.97 (s, 2 H), 4.33 (s, 2 H), 7.44 (d, 2 H), 7.74 (d, 2 H), 7.85 (d, 2 H), 7.91 (d, 2 H).

LRMS (Thermospray): 361.0 (M+2H$^+$).

Example 9
N-Hydroxy 2-({methyl[(4'-chlorobiphen-4-yl)methyl]amino}sulfonyl)acetamide

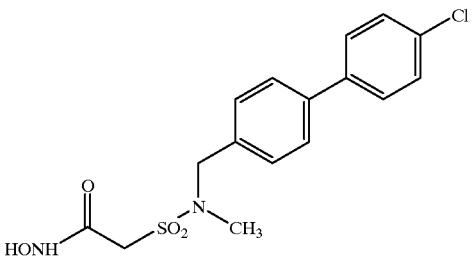

(a) Methyl-2-({methyl[(4'-chlorobiphen-4-yl)methyl]amino}sulfonyl)acetate

In a manner similar to Example 8 (b), methyl 2-({methyl[(4'-bromophenyl-4-yl)methyl]amino}sulfonyl)acetate (Example 8 (a)) was reacted with 4-chlorophenylboronic acid to give the titled compound as a pale yellow solid.

m.p. 103–106° C.

$^1$H NMR (400 MHz, CDCl$_3$): 2.87 (s, 3 H), 3.83 (s, 3 H), 4.04 (s, 2 H), 4.43 (s, 2 H), 7.38–7.46 (m, 4 H), 7.48–7.59 (m, 4 H).

LRMS (Thermospray): 385.2 (M+H$^+$)

(b) N-Hydroxy-2-({methyl[(4'-chlorobiphen-4-yl)methyl]amino}-sulfonyl)acetamide

In a manner similar to Example 1 (b), methyl-2-({methyl[(4'-chlorobiphenyl-4-yl)methyl]amino}sulfonyl)acetate was reacted with hydroxylamine to give the title compound as a colourless solid.

m.p. 158–161° C.

$^1$H NMR (400 MHz, DMSO-d$_6$): 2.72 (s, 3 H), 3.95 (s, 2 H), 4.32 (s, 2 H), 7.40 (d, 2 H), 7.49 (d, 2 H), 7.66 (d, 2 H), 7.69 (d, 2 H), 9.22 (s, 1 H), 10.83 (s, 1 H).

LRMS (Thermospray): 369.8 (M+H$^+$).

Example 10
N-Hydroxy 2-({methyl[3-(biphen-4-yl)-trans-prop-2-enyl]amino}sulfonyl) acetamide

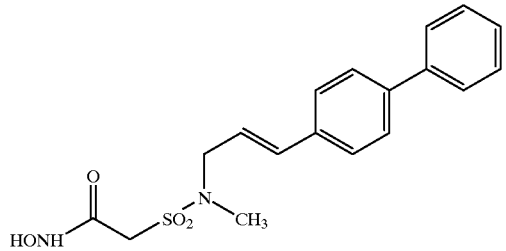

(a) Methyl 2-({methyl[allyl]amino}sulfonyl)acetate

In a manner similar to Example 1 (a), N-methyl-N-allylamine was reacted with methyl chiorosulfonylacetate to give the title compound as a pale yellow oil.

$^1$H NMR (400 MHz, CDCl$_3$): 2.89 (s, 3 H), 3.81 (s, 3 H), 3.81 (d, 2 H), 3.97 (s, 2 H), 5.03–5.15 (m, 2 H), 5.74–5.88 (m, 1 H).

(b) Methyl-2-({methyl[3-(biphen-4-yl)-trans-prop-2-enyl]amino}sulfonyl)acetate

To a solution of methyl 2-({methyl[allyl]amino}sulfonyl) acetate (300 mg, 1.4 mmol) and 4-bromobiphenyl (370 mg, 1.54 mmol) in acetonitrile (4 ml) was added triethylamine (0.3 ml, 2.1 mmol), palladium(II) acetate (17 mg, 0.07 mmol) and tri-ortho-tolyl phosphine (52 mg, 0.14 mmol)

and the solution was heated to reflux under an atmosphere of nitrogen for 3 hours. The mixture was cooled to ambient temperature, the solvent was evaporated and the residue was purified by flash chromatography on silica gel (dichloromethane as eluent) to give the title compound as a pale yellow solid (300 mg).

m.p. 104–107° C.

$^1$H NMR (300 MHz, CDCl$_3$): 2.97 (s, 3 H), 3.86 (s, 3 H), 4.00–4.13 (m, 4 H), 6.24 (dt, 1 H), 6.66 (d, 1 H), 7.33–7.40 (m, 1 H), 7.41–7.54 (m, 4 H), 7.58–7.71 (m, 4 H).

LRMS (Thermospray): 377.2 (MNH$_4^+$).

(c) N-Hvdroxy-2-({methyl[3-(biphen-4-yl)-trans-prop-2-enyl]amino}sulfonyl)-acetamide In a manner similar to Example 1 (b), methyl 2-({methyl [3-(1,1'-biphenyl-4-yl)-trans-prop-2-enyl]amino}sulfonyl) acetate was reacted with hydroxylamine to give the title compound as a colourless solid.

m.p. 153–155° C.

$^1$H NMR (300 MHz, DMSO-d$_6$): 2.82 (s, 3 H), 3.88–3.97 (m, 4 H), 6.34 (dt, 1 H), 6.66 (d, 1 H), 7.36 (d, 1 H), 7.43 (d, 1 H), 7.46 (d, 1 H), 7.56 (d, 2 H), 7.64 (d, 2 H), 7.67 (d, 2 H), 9.20 (s, 1 H), 10.81 (s, 1 H).

LRMS (Thermospray): 362.2 (M+2H$^+$).

Example 11
N-Hydroxy 2-({methyl[3-(biphen-4-yl)-prop-1-yl]amino}sulfonyl)acetamide

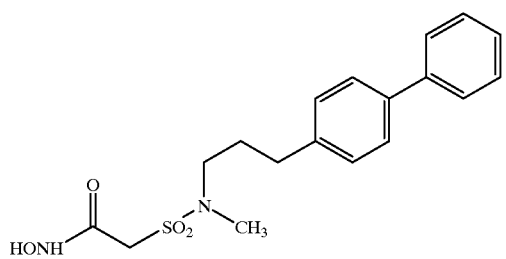

(a) Methyl- 2-({methyl[3-(biphen-4-yl)-propyl]amino}sulfonyl)acetate

To a solution of methyl- 2-({methyl[3-(biphen-4-yl)-trans-prop-2-enyl]amino}sulfonyl)acetate (Example 10 (b), 200 mg, 0.56 mmol) and ammonium formate (175 mg, 2.8 mmol) in methanol (5 ml) was added 20% palladium hydroxide on carbon (50 mg) and the mixture was heated to reflux for 4 hours. The mixture was cooled to ambient temperature, filtered through arbocel and the filtrate was concentrated under reduced pressure to give the title compound as a pale yellow solid (193 mg).

m.p. 66–70° C.

$^1$H NMR (300 MHz, CDCl$_3$): 1.89–2.04 (m, 2 H), 2.72 (t, 2 H), 2.95 (s, 3 H), 3.30 (t, 2 H), 3.80 (s, 3 H), 3.97 (s, 2 H), 7.23–7.38 (m, 3 H), 7.40–7.47 (m, 2 H), 7.54 (d, 2 H), 7.59 (d, 2 H).

LRMS (Thermospray): 379.2 (MNH$_4^+$).

(b) N-Hydroxy 2-({methyl[3-biphen-4-yl)-propyl]amino}sulfonyl)acetamide

In a manner similar to Example 1 (b), methyl-2-({methyl [3-(biphen-4-yl)-propyl]amino}sulfonyl)acetate was reacted with hydroxylamine to give the title compound as a colourless solid.

m.p. 137–140° C.

$^1$H NMR (300 MHz, DMSO-d$_6$): 1.75–1.93 (m, 2 H), 2.61 (t, 2 H), 2.82 (s, 3 H), 3.18 (t, 2 H), 3.83 (s, 2 H), 7.25–7.36 (m, 3 H), 7.40–7.50 (m, 2 H), 7.57 (d, 2 H), 7.64 (d, 2 H), 9.05–9.28 (br s, 1 H).

LRMS (Thermospray): 380.2 (MNH$_4^+$).

Example 12
N-Hydroxy 2-({methyl-[3-(2-methylbiphen-4-yl)-trans-prop-2-enyl]amino}-sulfonyl)acetamide

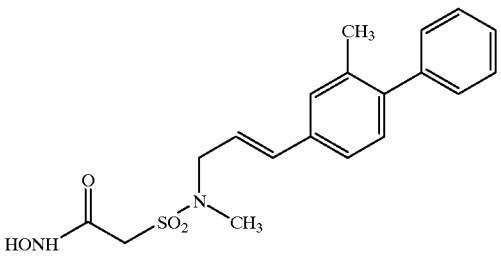

(a) Methyl 2-({methyl-[3-(2-methylbiphen-4-yl)-trans-prop-2-enyl]amino}sulfonyl)acetate In a manner similar to Example 10 (b), methyl 2-({methyl [allyl]amino}sulfonyl)acetate Example 10 (a)) was reacted with 4-bromo-2-methylbiphenyl (Preparation 7) to give the title compound as a pale yellow low melting solid.

$^1$H NMR (400 MHz, CDCl$_3$): 2.29 (s, 3 H), 2.97 (s, 3 H), 3.93 (s, 3 H), 4.00–4.07 (m, 4 H), 6.23 (dt, 1 H), 6.62 (d, 1 H), 7.18–7.47 (m, 8 H).

LRMS (Thermospray): 391.9 (MNH$_4^+$).

(b) N-Hydroxy 2-({methyl-[3-(2-methylbiphen-4-yl)-trans-prop-2-enyl]amino}-sulfonyl)acetamide In a manner similar to Example 1 (b), methyl-2-({methyl-[3-(2-methylbiphen-4-yl)-trans-prop-2-enyl] amino}sulfonyl)acetate was reacted with hydroxylamine to give the titled compound as a colourless solid.

m.p. 146–149° C.

$^1$H NMR (400 MHz, DMSO-d$_6$): 2.23 (s, 3 H), 2.81 (s, 3 H), 3.82–4.02 (m, 4 H), 6.33 (dt, 1 H), 6.62 (d, 1 H), 7.17 (d, 1 H), 7.25–7.49 (m, 7 H), 9.21 (s, 1 H), 10.82 (s, 1 H).

LRMS (Thermospray): 376.1 (M+2H$^+$)

Preparation 1

N-Methyl-N-[(biphen-4-yl)methyl]amine

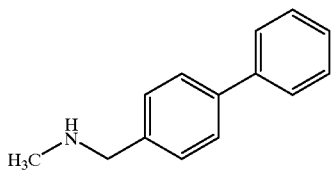

To a solution of biphenyl-4-carboxaldehyde (4.6 g, 25 mmol) in ethanol (50 ml) was added methylamine (3.0 ml of 33% solution in ethanol, 25 mmol) and acetic acid (1.4 ml, 25 mmol), and the mixture was stirred under an atmosphere of nitrogen. After 20 minutes sodium tri(acetoxy) borohydride (10.5 g, 50 mmol) was added and stirring was continued for 16 hours. The mixture was diluted with 2 M aqueous hydrochloric acid (200 ml) and washed with ethyl acetate (3×100 ml). The aqueous layer was basified to pH 12 with concentrated aqueous ammonia solution and extracted with dichloromethane (4×100 ml). The combined organic layers were dried (Na$_2$SO$_4$) and the solvent was evaporated under reduced pressure to give the title compound as a pale yellow oil (2.5 g).

$^1$H NMR (300 MHz, CDCl$_3$):1.38 (br s, 1 H), 2.50 (s, 3 H), 3.80 (s, 2 H), 7.30–7.48 (m, 5 H), 7.52–7.64 (m, 4 H).

Preparation 2
2-(Biphen-4-yl)ethylamine

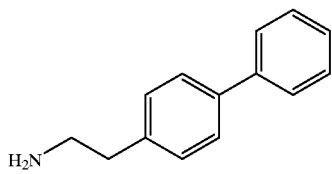

This was prepared according to the method described by W. W. Zacac Jr, J. F. Siuda, M. J. Nolan and T. M. Santususso, in *J. Org. Chem.* 1971, 36, 3539.

Preparation 3
2-(Biphen-4-yloxy)ethylamine

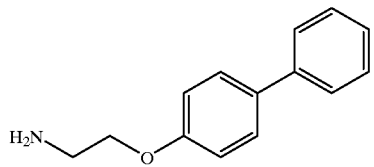

(a) 2-([Biphen-4-yloxy]ethyl)isoindoline-1,3-dione

Potassium phthalimide (1.2 g, 6.5 mmol) was added to a solution of 4-(2-chloroethoxy)-1,1'-biphenyl (1.0 g, 5.4 mmol) in anhydrous dimethylformarnmide (3 ml) and anhydrous dimethylsulfoxide (3 ml) and the mixture was heated to 70° C. under an atmosphere of nitrogen for 5 hours. The mixture was cooled to ambient temperature and partitioned between water and dichloromethane. The organic layer was washed with water, dried ($Na_2SO_4$) and the solvent was evaporated under reduced pressure to give the title compound as a colourless solid (1.51 g).

$^1$H NMR (300 MHz, $CDCl_3$): 4.13 (t, 2 H), 4.26 (t, 2 H), 6.96 (d, 2 H), 7.23–7.34 (m, 1 H), 7.34–7.44 (m, 2 H), 7.44–7.58 (m, 4 H), 7.67–7.80 (m, 2 H), 7.83–7.93 (m, 2 H).

LRMS (Thermospray): 343.3 ($M^+$).

(b) 2-(Biphen-4-yloxy)ethylamine

To a solution of 2-([biphen-4-yloxy]ethyl)isoindoline-1,3-dione (1.5 g, 4.4 mmol) in dichloromethane (30 ml) was added methylarnine (33% solution in ethanol, 50 ml) and the solution was heated to reflux under an atmosphere of nitrogen for 2 hours. The mixture was cooled to ambient temperature, and the solvent was evaporated under reduced pressure. The residue was purified by flash chromatography on silica gel (dichloromethane/methanol/aqueous ammonium solution 95:5:0 to 94:5:1 as eluent) to give the title compound as a colourless solid (505 mg).

$^1$H NMR (400 MHz, $CDCl_3$): 1.40 (s, 2 H), 3.05–3.19 (m, 2 H), 3.98–4.12 (m, 2 H), 6.98 (d, 2 H), 7.22–7.66 (m, 7 H).

LRMS (Thermospray): 214.0 ($MH^+$).

Preparation 4
N-Methyl-N-(4-phenoxybenzyl)amine

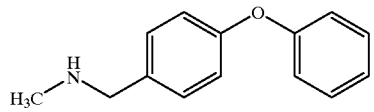

To a solution of 4-phenoxybenzaldehyde (4.4 ml, 25 mmol) in ethanol (50 ml) was added methylamine (3.0 ml of 33% solution in ethanol, 25 mmol) and acetic acid (1.4 ml, 25 mmol), and the mixture was stirred under an atmosphere of nitrogen. After 20 minutes sodium tri(acetoxy) borohydride (10.5 g, 50 mmol) was added and stirring was continued for 16 hours. The mixture was diluted with 2 M aqueous hydrochloric acid (200 ml) and washed with diethyl ether (2×100 ml). The aqueous layer was basified to pH 12 with concentrated aqueous ammonia solution and extracted with dichloromethane (4×100 ml). The combined organic layers were dried ($Na_2SO_4$), the solvent was evaporated under reduced pressure and the residue was purified by flash chromatography on silica gel (dichloromethane/methanol/aqueous ammonia solution 95:5:0 to 94:5:1) to give the titled compound as a colourless oil (3.3 g).

$^1$H NMR (300 MHz, $CDCl_3$): 2.33 (s, 1 H), 2.47 (s, 3 H), 3.73 (s, 2 H), 6.93–7.02 (m, 4 H), 7.02–7.13 (m, 1 H), 7.23–7.37 (m, 4 H).

Preparation 5
N-Methyl-N-(4-bromobenzyl)amine

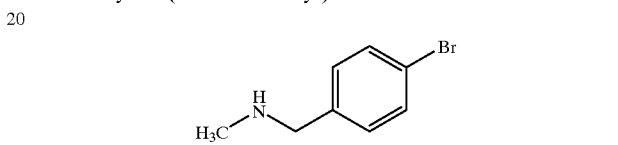

This was prepared according to the method of G. M. Singer et al, described in *J Med.*

Chem. 1986, 29, 40.

Preparation 6
4-Cyano-phenylboronic acid

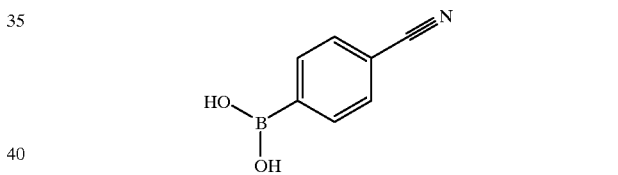

This was prepared according to the method of G. J. Pernia et al, described in *J. Am. Chem. Soc.* 1996, 118, 10220.

Preparation 7
4-Bromo-2-methylbiphenyl

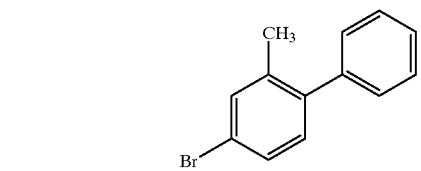

This was prepared according to the method of M. Gomberg et al, described in *J Am Chem. Soc.* 1926, 48, 1372.

Biological Data

The substances of Examples 1–12 had MMP-3 $IC_{50}$ values of 1.5 µM or less. The substances of Examples 1–12 had MMP-2 $IC_{50}$ values of 6.3 µM or less. Certain of the substances of the Examples had MMP-13 $IC_{50}$ values of 0.05 µM or less.

We claim:

1. A compound of formula (I):

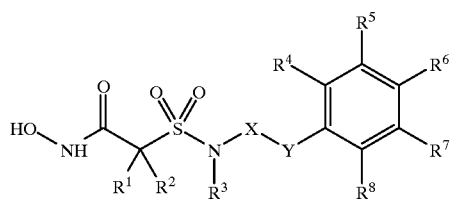

(I)

and a pharmaceutically- and/or veterinarily-acceptable salt thereof, and a solvate of such compound and salt, wherein $R^1$ and $R^2$ are each independently H, $C_{2-6}$ alkenyl, aryl($C_{1-6}$ alkyl), heteroaryl($C_{1-6}$ alkyl), aryloxy($C_{,4}$ alkyl), heteroaryloxy-($C_{1-6}$ alkyl), $C_{1-6}$ alkyl optionally substituted by $NH_2$, $C_{2-6}$ acylamino, OH, or by $CO_2H$, or $R^1$ and $R^2$ can be taken together with the carbon atom to which they are attached, to form a 4- to 8-membered saturated carbocyclic or heterocyclic ring, which heterocyclic ring has 1 or 2 hetero-groups selected from O, $S(O)_n$ or $NR^9$ in the ring, $R^3$ is H, $C_{1-6}$ alkyl or ($C_{1-6}$ alkoxy)$C_{1-6}$ alkyl, $R^4$, $R^5$, $R^7$ and $R^8$ are each independently H, $C_{1-6}$ alkyl, $C_{1-6}$ alkoxy, CN or halogen, $R^6$ is H, aryl, heteroaryl, aryloxy or heteroaryloxy, $C_{1-6}$ alkyl, $C_{1-6}$ alkoxy, CN or halogen, $R^9$ is H or $C_{1-6}$ alkyl, n is 0, 1 or 2, X is $C_{1-6}$ alkylene or $C_{2-6}$ alkenylene, Y is a direct link, CH=CH or O, wherein "aryl" is phenyl optionally fused with another ring selected from furan, dioxolan, and pyran, which group is optionally mono- or disubstituted by substituents independently seleceted from halogen, CN, $C_{1-6}$ alkyl optionally substituted by OH or $NH_2$, $C_{1-6}$ alkoxy, perfluoro($C_{1-6}$ alkyl) and perfluoro($C_{1-6}$ alkoxy), and wherein "heteroaryl" is a 5- or 6-membered aromatic heterocycle with one or two heteroatoms in the ring, which heteroatoms are independently selected from O, N and S, which heteroaryl is optionally mono- or disubstituted by substituents independently selected from halogen, CN, $C_{1-6}$ alkyl optionally substituted by OH or $NH_2$, $C_{1-6}$ alkoxy, perfluoro($C_{1-6}$ alkyl) and perfluoro($C_{1-6}$ alkoxy).

2. A compound according to claim 1 wherein $R^1$ is H.

3. A compound according to claim 1 wherein $R^2$ is H.

4. A compound according to claim 1 wherein $R^3$ is H or $C_{1-6}$ alkyl.

5. A compound according to claim 1 wherein $R^4$ is H.

6. A compound according to claim 1 wherein $R^5$ is H or $C_{1-6}$ alkyl.

7. A compound according to claim 1 wherein $R^6$ is H, $aryl^1$ or $aryl^1$oxy wherein "$aryl^1$" is phenyl optionally mono- or disubstituted by substituents selected from halogen and CN.

8. A compound according to claim 1 wherein $R^7$ is H.

9. A compound according to claim 1 wherein $R^8$ is H.

10. A compound according to claim 1 wherein X is $CH_2$, $(CH_2)_2$, $(CH_2)_3$, or is $CH_2CH=CH$ wherein the terminal methinyl carbon of this group is linked to the Y moiety.

11. A compound according to claim 1 wherein $R^3$ is H or $CH_3$.

12. A compound according to claim 1 wherein $R^5$ is H or $CH_3$.

13. A compound according to claim 1 wherein $R^6$ is H, $aryl^2$ or $aryl^2$oxy herein "$aryl^2$" is phenyl optionally 4-substituted by substituents selected from Cl and CN.

14. A compound according to claim 1 wherein $R^6$ is H, phenyl, phenoxy, 4-cyanophenyl or 4-chlorophenyl.

15. A compound according to claim 1 wherein at least two of the groups $R^4$, $R^5$, $R^7$ and $R^8$ are all H.

16. A compound according to claim 1 wherein $R^4$, $R^7$ and $R^8$ are all H and $R^5$ is $CH_3$.

17. A compound according to claim 1 wherein $R^1$, $R^2$, $R^4$, $R^7$ and $R^8$ are all H, $R^3$ is H or $CH_3$, $R^5$ is H or $CH_3$, $R^6$ is H, phenyl, phenoxy, 4-cyanophenyl or 4-chlorophenyl, X is $CH_2$, $(CH_2)_2$, $(CH_2)_3$, or is $CH_2CH=CH$ wherein the terminal methine carbon of this group is linked to the Y moiety, and the salts and solvates thereof.

18. A pharmaceutical composition comprising a substance according to claim 1, together with a pharmaceutically acceptable diluent or carrier.

19. A veterinary composition comprising a substance according to claim 1, together with a veterinarally acceptable diluent or carrier.

20. A method of treating a condition mediated by one or more MMPs, in an animal such as a mammal (including a human being), which comprises administering to said animal an effective amount of a substance according to claim 1.

21. A method of treating atherosclerotic plaque rupture, myocardial infarction, heart failure, restenosis, stroke, periodontal disease, tissue ulceration, wounds, skin diseases, cancer metastasis, tumour angiogenesis, age-related macular degeneration, fibrotic disease, rheumatoid arthritis, osteoarthritis and inflammatory diseases dependent on migratory inflammatory cells, in an animal such as a mammal (including a human being), which comprises administering to said animal an effective amount of a substance according to claim 1.

* * * * *

UNITED STATES PATENT AND TRADEMARK OFFICE
CERTIFICATE OF CORRECTION

PATENT NO. : 6,090,852
DATED : July 18, 2000
INVENTOR(S) : Kevin Neil Dack and Gavin Alistair Whitlock It is certified that error appears in the above-identified patent and that said Letters Patent is hereby corrected as shown below:

<u>Column 1,</u>
Line 3, prior to the first sentence of text, add the following sentence:
-- This application claims priority from application GB 9801690.0, filed January 27, 1998. --

Signed and Sealed this

Nineteenth Day of March, 2002

Attest:

JAMES E. ROGAN
Attesting Officer          Director of the United States Patent and Trademark Office